US009161861B2

(12) United States Patent
Sakaguchi et al.

(10) Patent No.: US 9,161,861 B2
(45) Date of Patent: Oct. 20, 2015

(54) APPARATUS AND METHOD OF MANUFACTURING AN ABSORBENT ARTICLE

(75) Inventors: Satoru Sakaguchi, Kagawa (JP); Yoshikazu Ogasawara, Kagawa (JP); Noriaki Ito, Kagawa (JP); Tomomi Oku, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 885 days.

(21) Appl. No.: 13/394,840

(22) PCT Filed: Sep. 10, 2010

(86) PCT No.: PCT/JP2010/065581
§ 371 (c)(1),
(2), (4) Date: May 2, 2012

(87) PCT Pub. No.: WO2011/033995
PCT Pub. Date: Mar. 24, 2011

(65) Prior Publication Data
US 2012/0208688 A1 Aug. 16, 2012

(30) Foreign Application Priority Data
Sep. 18, 2009 (JP) .................................. 2009-217910

(51) Int. Cl.
B31B 1/26 (2006.01)
B31B 3/02 (2006.01)
A61F 13/15 (2006.01)

(52) U.S. Cl.
CPC ..... *A61F 13/15756* (2013.01); *A61F 13/15804* (2013.01)

(58) Field of Classification Search
CPC ... A61F 13/15747; A61F 13/15; A61F 13/49; A61F 13/5622; A61F 13/565
USPC .......................... 493/162, 177–180, 201, 246
See application file for complete search history.

(56) References Cited

U.S. PATENT DOCUMENTS 3,929,134 A * 12/1975 Karami .......................... 604/378
6,723,035 B2 * 4/2004 Franklin et al. ............... 493/450
(Continued)

FOREIGN PATENT DOCUMENTS

JP 1132803 A 5/1989
JP H01132803 A 5/1989
(Continued)

OTHER PUBLICATIONS

International Search Report for PCT/JP2010/065581 dated Nov. 30, 2010.
(Continued)

*Primary Examiner* — Stephen F Gerrity
*Assistant Examiner* — Eyamindae Jallow
(74) *Attorney, Agent, or Firm* — Hauptman Ham, LLP

(57) ABSTRACT

A method of manufacturing an absorbent article includes forming a pair of side flap-folded sections by folding a continuous sheet such that end sections in a width direction of the continuous sheet are folded inwardly in the width direction, while the continuous sheet is being transported in a continuous direction of the continuous sheet, producing a flap segment by segmenting the continuous sheet at a predetermined pitch in the continuous direction, joining the flap segment to a continuous body of absorbent main bodies in an overlapped manner, while the continuous body of absorbent main bodies is being transported in a transport direction corresponding to a continuous direction of the continuous body, and dividing the flap segment into a section having the pair of first side flaps and a section having the pair of second side flaps by segmenting the continuous body of absorbent main bodies.

7 Claims, 8 Drawing Sheets

(56) References Cited

U.S. PATENT DOCUMENTS

| | | | |
|---|---|---|---|
| 6,962,578 B1* | 11/2005 | LaVon | 604/385.16 |
| 7,500,941 B2* | 3/2009 | Coe et al. | 493/438 |
| 8,696,343 B2* | 4/2014 | Yamamoto | 425/335 |
| 2003/0119641 A1* | 6/2003 | Reising | 493/394 |
| 2003/0120240 A1* | 6/2003 | Buell et al. | 604/385.01 |
| 2004/0236299 A1* | 11/2004 | Tsang et al. | 604/385.24 |
| 2005/0020991 A1* | 1/2005 | Van Gompel et al. | 604/385.01 |
| 2005/0065491 A1* | 3/2005 | Schneider et al. | 604/385.01 |
| 2005/0148974 A1* | 7/2005 | Datta et al. | 604/385.01 |
| 2005/0171499 A1* | 8/2005 | Nigam et al. | 604/385.22 |
| 2005/0215972 A1* | 9/2005 | Roe et al. | 604/385.29 |
| 2006/0036229 A1* | 2/2006 | Rohrl | 604/389 |
| 2007/0016158 A1* | 1/2007 | Endres et al. | 604/389 |
| 2007/0118091 A1* | 5/2007 | LaVon et al. | 604/392 |
| 2007/0142194 A1* | 6/2007 | Coenen et al. | 493/405 |
| 2007/0287980 A1* | 12/2007 | Kline et al. | 604/385.24 |
| 2009/0098995 A1* | 4/2009 | Burns et al. | 493/440 |
| 2009/0105682 A1* | 4/2009 | Kouno et al. | 604/385.04 |
| 2009/0124991 A1* | 5/2009 | Tsang et al. | 604/385.23 |
| 2009/0126864 A1* | 5/2009 | Tachibana et al. | 156/216 |
| 2009/0204093 A1* | 8/2009 | Vasic et al. | 604/385.23 |
| 2009/0312738 A1* | 12/2009 | LaVon et al. | 604/385.28 |
| 2010/0065199 A1 | 3/2010 | Hormung et al. | |
| 2010/0168706 A1* | 7/2010 | Vasic | 604/378 |
| 2011/0288517 A1* | 11/2011 | Mori | 604/385.3 |
| 2012/0208688 A1* | 8/2012 | Sakaguchi et al. | 493/343 |
| 2012/0225764 A1* | 9/2012 | Ogasawara | 493/405 |
| 2012/0296303 A1* | 11/2012 | Ng et al. | 604/378 |
| 2012/0302417 A1* | 11/2012 | Gouda et al. | 493/346 |
| 2013/0053811 A1* | 2/2013 | Umebayashi | 604/385.03 |
| 2013/0110073 A1* | 5/2013 | Umebayashi | 604/385.16 |
| 2013/0184137 A1* | 7/2013 | Umebayashi | 493/343 |
| 2013/0296152 A1* | 11/2013 | Murakami et al. | 493/405 |

FOREIGN PATENT DOCUMENTS

| | | |
|---|---|---|
| JP | 4261655 A | 9/1992 |
| JP | 9070414 A | 3/1997 |
| JP | 2005000296 A | 1/2005 |
| JP | 2006102022 A | 4/2006 |
| JP | 2008079827 A | 4/2008 |
| WO | 2007004640 A1 | 1/2007 |
| WO | 2008141834 A1 | 11/2008 |

OTHER PUBLICATIONS

Corresponding Chinese Application No. 2009-217910 Office Action dated Jun. 19, 2013.
Office Action issued Oct. 9, 2014, corresponding to Philippines patent application No. 1/2012/500447.

* cited by examiner

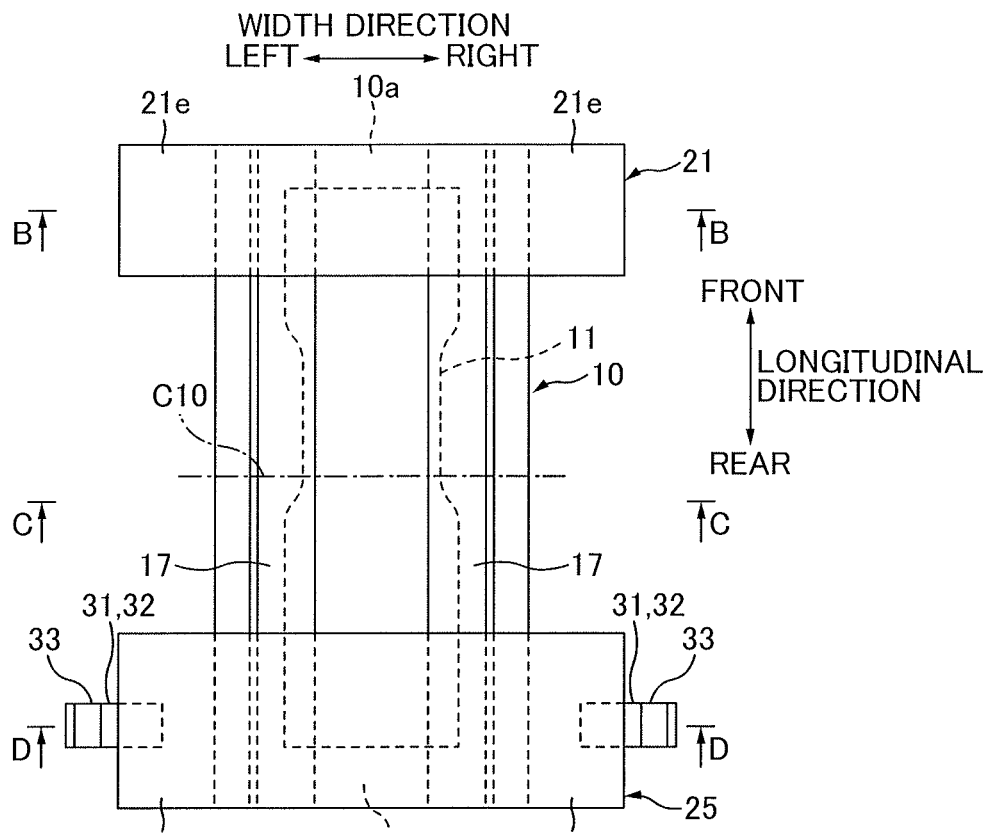
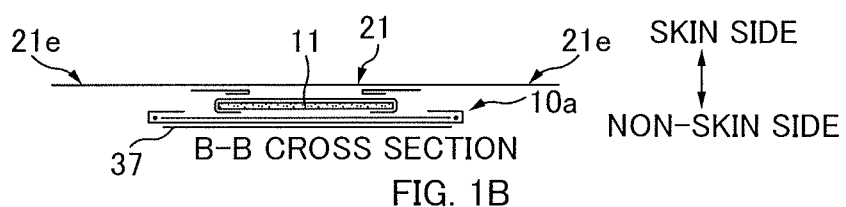
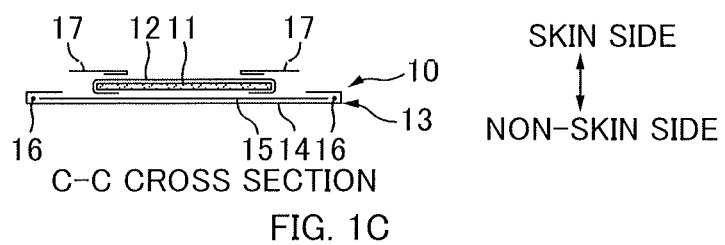
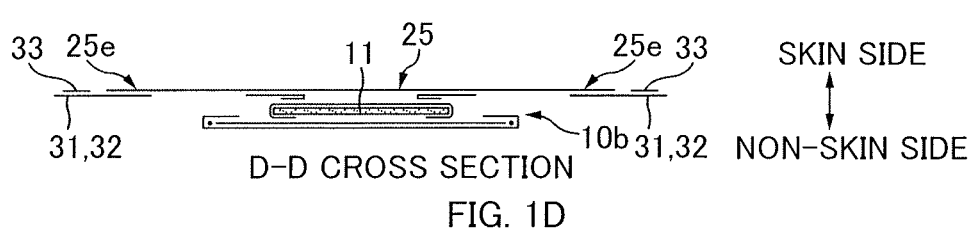

APPARATUS AND METHOD OF MANUFACTURING AN ABSORBENT ARTICLE

RELATED APPLICATIONS

The present application is a National Phase of International Application Number PCT/JP2010/065581, filed Sep. 10, 2010, and claims priority from, Japanese Application Number 2009-217910, filed Sep. 18, 2009.

TECHNICAL FIELD

The present invention relates to an apparatus and method of manufacturing an absorbent article such as a disposable diaper.

BACKGROUND ART

A disposable diaper is known as an absorbent article that absorbs excretory fluid. One type of such an absorbent article is a so-called open type diaper. The opentype diaper includes an absorbent main body that is placed against a wearer's crotch where each end section of the absorbent main body in a longitudinal direction is provided with a pair of left and right side flaps that are formed to protrude in a width direction. In the use of such a diaper, the diaper is put on a wearer by pulling the diaper to the left and right in the width direction with the left and right side flaps.

Patent literatures 1 and 2 disclose a method of manufacturing such an open type diaper. In other words, there is a description that respective side flaps at the left and right in the width direction are cutout as mutually separate members and each side flap is individually joined to each of the left and right side section (each end section in the width direction) of a continuous body of absorbent main bodies that continues in a transport direction.

CITATION LIST

Patent Literature

Patent Literature 1: JP-A-04-261655
Patent Literature 2: JP-A-2006-102022

DISCLOSURE OF INVENTION

Problems to be Solved by the Invention

However, with such manufacturing methods, a diaper having a low tensile strength in the width direction may be manufactured. That is to say, as has been described above, the left and right side flaps in this case are mutually separate members and each of them is independently joined to the absorbent main body. Accordingly, the tensile strength in the width direction of the diaper depends on the joining strength between the absorbent main body and the side flaps, and in a case where the joining strength is weak, the diaper may easily split at a joining section between the side flap and the absorbent main body when the diaper is pulled in the width direction at the time of wearing.

Therefore, in terms of the tensile strength of the diaper in the width direction, rather than the mutually independent two members as described above, it is more preferable that the left and right side flaps are provided as a single member that continues in the width direction, since a tensile force at the time of putting the diaper on can also be counteracted by the material strength of the side flap.

Also, in the case of the above-mentioned manufacturing methods, since the side flaps are joined only at side sections of the absorbent main body (end sections in a width direction), their joining areas are small. As a result, the side flaps may fall off from the continuous body of absorbent main bodies while being transported after the joining to the continuous body of absorbent main bodies, and production may become unstable.

Further, as described in Patent Literature 1, after the joining to the continuous body of absorbent main bodies, in the case where the side flaps intermittently protrudes outwardly in the width direction from the continuous body of absorbent main bodies, the side flaps may flutter while being transported integrally with the continuous body of absorbent main bodies. This may cause problems such as being caught in various devices in the vicinity of the transport path, and thus production may become unstable.

Also, depending on the production line, there is a case in which an amount of meandering during the transport of the continuous body of absorbent main bodies is detected at a position of an end edge of the continuous body in the width direction. In such a case, it is likely that the amount of meandering is falsely detected due to the fluttering of the above-mentioned side flaps and production may become unstable due to unnecessary emergency stop operations and the like.

With regards to such false detection of the amount of meandering, the method described in Patent Literature 2 has a similar drawback. In detail, Patent Literature 2 discloses that left and right side flaps are joined to the continuous body of absorbent main bodies in a state of an overlapped body in which the side flaps are temporarily overlapped with each other by a fastening tape. It is also illustrated that the width of the overlapped body has the same size as the width of the continuous body of absorbent main bodies. However, in such a case where the widths are mutually of the same size, if the position at which the continuous body of absorbent main bodies is joined to the above-mentioned overlapped body becomes offset from the target position in the width direction, an end edge of the overlapped body will protrude outwardly beyond an end edge of the continuous body of absorbent main bodies in the width direction. As a result, there is a possibility that the amount of meandering is falsely detected by falsely recognizing the end edge of the overlapped body as an end edge of the continuous body of the absorbent main bodies.

Also, in the manufacturing methods of Patent Literatures 1 and 2, as has been described above, since the left and right side flaps are mutually separate members, the process of joining these side flaps to the continuous body of absorbent main bodies may be a joining process that needs to be performed once for each of the left and right as described in Patent Literature 1, or, may include a single process of joining to the continuous body of the absorbent main bodies but instead requires a separate process of temporarily overlapping the left and right side flaps into a state of the above-mentioned overlapped body as described in Patent Literature 2. In other words, in either of the Patent Literature 1 and 2, a process similar to an overlapping process needs to be performed twice, and thus the manufacturing process is cumbersome.

An advantage of some aspects of the invention is to provide a manufacturing method and a manufacturing apparatus of an absorbent article that are capable of manufacturing an absorbent article having a high tensile strength in a width direction and are also capable of stabilizing production and simplifying the manufacturing process.

Means for Solving the Problems

The main aspect of the invention is:

a method of manufacturing an absorbent article including an absorbent main body, a pair of first side flaps and a pair of second side flaps, the absorbent main body having an absorbent body that absorbs fluid, the absorbent main body being placed against the crotch of a wearer, the pair of first side flaps being provided at one end section of the absorbent main body in a longitudinal direction, the first side flaps being folded in an outwardly projectable manner in a width direction of the absorbent main body from respective end edges of the absorbent main body in the width direction, the pair of second side flaps being provided at the other end section of the absorbent main body in the longitudinal direction, the second side flaps being folded in an outwardly projectable manner in the width direction of the absorbent main body from respective end edges of the absorbent main body in the width direction, the method including:

forming a pair of side flap-folded sections by folding a continuous sheet in such a manner that end sections in a width direction of the continuous sheet are folded inwardly in the width direction, respectively, while the continuous sheet that is a base material of the first side flap and the second side flap is being transported in a continuous direction of the continuous sheet;

producing a flap segment by segmenting the continuous sheet at a predetermined pitch in the continuous direction, the continuous sheet having the pair of side flap-folded sections formed thereon;

joining the flap segment to a continuous body of absorbent main bodies in an overlapped manner with the flap segment lying across a border position between the absorbent main bodies adjacent to each other in the transport direction, while the continuous body that includes the absorbent main bodies continuing in the longitudinal direction is being transported in a transport direction that corresponds to a continuous direction of the continuous body; and dividing the flap segment into a section having the pair of first side flaps and a section having the pair of second side flaps by segmenting the continuous body of absorbent main bodies at the border position with the flap segment being joined to the continuous body of absorbent main bodies.

A further aspect of the invention is:

an apparatus that manufactures an absorbent article including an absorbent main body, a pair of first side flaps and a pair of second side flaps, the absorbent main body having an absorbent body that absorbs fluid, the absorbent main body being placed against the crotch of a wearer, the pair of first side flaps being provided at one end section of the absorbent main body in a longitudinal direction, the first side flaps being folded in an outwardly projectable manner in a width direction of the absorbent main body from respective end edges of the absorbent main body in the width direction, the pair of second side flaps being provided at the other end section of the absorbent main body in the longitudinal direction, the second side flaps being folded in an outwardly projectable manner in the width direction of the absorbent main body from respective end edges of the absorbent main body in the width direction, the apparatus including:

a first device that forms a pair of side flap-folded sections by folding a continuous sheet in such a manner that end sections in a width direction of the continuous sheet are folded inwardly in the width direction, respectively, while the continuous sheet that is a base material of the first side flap and the second side flap is being transported in a continuous direction of the continuous sheet;

a second device that produces a flap segment by segmenting the continuous sheet at a predetermined pitch in the continuous direction, the continuous sheet having the pair of side flap-folded sections formed thereon;

a third device that joins the flap segment to a continuous body of absorbent main bodies in an overlapped manner with the flap segment lying across a border position between the absorbent main bodies adjacent to each other in the transport direction, while the continuous body that includes the absorbent main bodies continuing in the longitudinal direction is being transported in a transport direction that corresponds to a continuous direction of the continuous body; and a fourth device that divides the flap segment into a section having the pair of first side flaps and a section having the pair of second side flaps by segmenting the continuous body of absorbent main bodies at the border position with the flap segment being joined to the continuous body of absorbent main bodies.

Other aspects of the invention will be disclosed in this specification and accompanying drawings.

Advantageous Effects of the Invention

According to an aspect of the invention, a manufacturing method and a manufacturing apparatus of an absorbent article can be provided that are capable of manufacturing an absorbent article having a high tensile strength in a width direction and are also capable of stabilizing production and simplifying the manufacturing process.

BRIEF DESCRIPTION OF DRAWINGS

FIG. 1A is a plan view of a disposable diaper 1 in an open state.

FIGS. 1B to 1D are cross sectional views taken along B-B, C-C, and D-D in FIG. 1A, respectively.

FIG. 8A corresponds to a cross sectional view taken along B-B in FIG. 1A and FIG. 8B corresponds to a cross sectional view taken along D-D in FIG. 1A.

MODE FOR CARRYING OUT THE INVENTION

Figure 2:
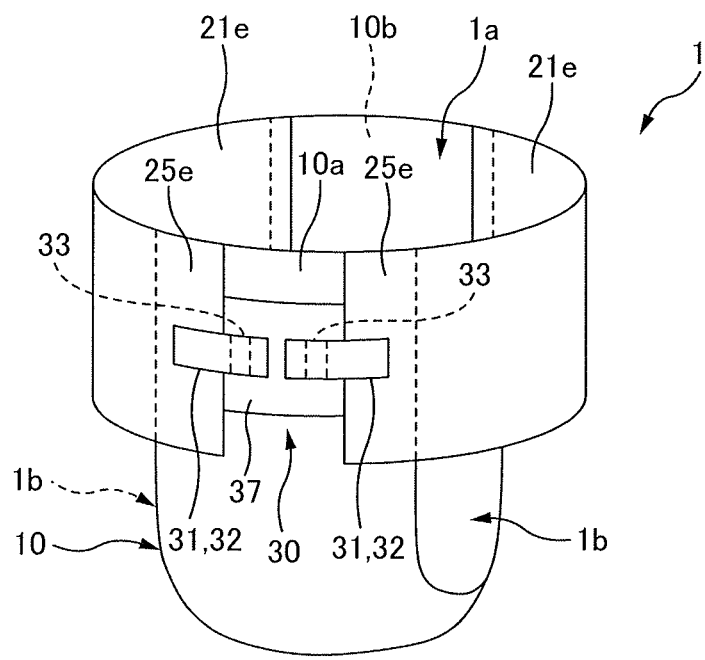
FIG. 2 is a perspective view of the disposable diaper 1 in a worn state.

At least the following matters will be disclosed in the present specification and accompanying drawings.

A method of manufacturing an absorbent article including an absorbent main body, a pair of first side flaps and a pair of second side flaps, the absorbent main body having an absorbent body that absorbs fluid, the absorbent main body being placed against the crotch of a wearer, the pair of first side flaps being provided at one end section of the absorbent main body in a longitudinal direction, the first side flaps being folded in an outwardly projectable manner in a width direction of the absorbent main body from respective end edges of the absorbent main body in the width direction, the pair of second side flaps being provided at the other end section of the absorbent main body in the longitudinal direction, the second side flaps being folded in an outwardly projectable manner in the width direction of the absorbent main body from respective end edges of the absorbent main body in the width direction, the method including:

forming a pair of side flap-folded sections by folding a continuous sheet in such a manner that end sections in a width direction of the continuous sheet are folded inwardly in the width direction, respectively, while the continuous sheet that is a base material of the first side flap and the second side flap is being transported in a continuous direction of the continuous sheet;

producing a flap segment by segmenting the continuous sheet at a predetermined pitch in the continuous direction, the continuous sheet having the pair of side flap-folded sections formed thereon;

joining the flap segment to a continuous body of absorbent main bodies in an overlapped manner with the flap segment lying across a border position between the absorbent main bodies adjacent to each other in the transport direction, while the continuous body that includes the absorbent main bodies continuing in the longitudinal direction is being transported in a transport direction that corresponds to a continuous direction of the continuous body; and dividing the flap segment into a section having the pair of first side flaps and a section having the pair of second side flaps by segmenting the continuous body of absorbent main bodies at the border position with the flap segment being joined to the continuous body of absorbent main bodies.

According to such method of manufacturing an absorbent article, the pair of first side flaps is a part of the flap segment produced from the continuous sheet. In other words, both first side flaps of the pair of first side flaps belong to the same material that continues in a width direction. Further, the pair of second side flaps is also a part of the flap segment produced from the continuous sheet. In other words, both second side flaps of the pair of second side flaps belong to the same material that continues in a width direction.

Therefore, at the time of wearing, no matter which side flap of the first side flaps and the second side flaps is to be pulled in the width direction, a tensile force in the width direction that acts on the absorbent article at that time can be counteracted with a tensile strength in the width direction of the flap segment that is the same material. As a result, the tensile strength in the width direction of the absorbent article can be improved.

Also, according to the above-mentioned manufacturing method, the flap segment is arranged across the absorbent main body in its width direction. Therefore, the joining region to the absorbent main body can be obtained widely in the width direction and thus problems such as peeling off of the flap segment that may occur during the transportation after the joining to the continuous body of absorbent main bodies can be effectively avoided. As a result, production can be stabilized.

Further, since both end sections of the flap segment are folded inwardly in the width direction based on the side flap-folded section, an amount of protrusion of the flap segment protruding outwardly from the continuous body of absorbent main bodies can be reduced or totally eliminated. Thus, problems such as both end sections of the flap segment being caught by various devices in the vicinity of the transport path can be reduced. This also contributes to stabilization of production.

Further, as has been described above, since both end sections of the flap segment are folded inwardly in the width direction, the total width of the flap segment after being folded can be made smaller than the total width of the continuous body of absorbent main bodies depending on the choice of a folding method. In this manner, even if the joining position of the flap segment to the absorbent main body is slightly offset from a target position in the width direction, it becomes difficult for the flap segment to project outwardly from both end edges of the continuous body of absorbent main bodies in the width direction. Thus, a false detection in a case of detecting an amount of meandering based on a position of an end edge of the continuous body of absorbent main bodies can be effectively suppressed. As a result, production can be stabilized.

Further, the forming of the side flap-folded sections can be performed by folding both end sections in the width direction while in the state of a continuous sheet. Accordingly, using a known configuration of devices such as a continuous fold plate device, the side flap-folded sections can be formed easily and in a stable manner. This also contributes to stabilization of production.

According to the above-mentioned manufacturing method, the joining of the pair of first side flaps and the pair of second side flaps to the continuous body of absorbent main bodies can be performed at once by the joining of the flap segment. Therefore, the number of joining processes to the continuous body of absorbent main bodies can be reduced and thus the manufacturing process can be simplified.

With such method of manufacturing an absorbent article, it is preferable that, in the joining of the flap segment to the continuous body of absorbent main bodies in an overlapped manner, the flap segment is joined to the continuous body of absorbent main bodies with each side flap-folded section of the pair of side flap-folded sections being made to correspond to each end section of the absorbent main body in the width direction, and the size of the flap segment in the width direction in a contracted width state in which the side flap-fold sections are folded is smaller than the size of the continuous body of absorbent main bodies in the width direction.

According to such a method of manufacturing an absorbent article, based on the contracted width state, both end edges of the flap segment in the width direction can be positively placed inward of both end edges of the absorbent main body in the width direction. Therefore, the above-mentioned problems such as being caught and a false detection of a meandering amount can be positively prevented.

With such method of manufacturing an absorbent article, it is preferable that, between the forming of the side flap-folded sections and the producing of the flap segment, faces that overlap each other at the side flap-folded section are temporarily joined in such a manner that the side flap-folded section is maintained in a folded state.

According to such a method of manufacturing an absorbent article, the side flap-folded sections can be positively prevented from fluttering during the transportation of the flap segment and problems such as the side flaps being caught by various devices in the vicinity of the transport path can be positively prevented.

With such method of manufacturing an absorbent article, it is preferable that, the pair of side flap-folded sections is formed in such a manner that a gap is provided between the side flap-folded sections regarding the width direction and that the side flap-folded sections open to a side opposite to the continuous body of absorbent main bodies, and that the method further includes, between the forming of the side flap-folded sections and the producing of the flap segment, providing a hook member of a fastening tape in correspondence with each side flap-folded section of the pair of side flap-folded sections, the hook member being protruded up to a position in the gap that is inner to the side flap-folded section in the width direction, the side flap-folded section being constrained in a folded state by an engagement of the hook member to a portion of the flap segment that is facing the gap.

According to such a method of manufacturing an absorbent article, the side flap-folded sections can be positively prevented from fluttering during the transport of the flap segment, and problems such as the side flaps being caught by various devices in the vicinity of the transport path can be positively prevented.

With such method of manufacturing an absorbent article, it is preferable that, the fastening tape includes a band-like tape base material and a hook member that is secured on the tape base material, the fastening tape before use being a connected body in which the tape base material of one of the folded sections of the pair of side flap-folded sections and the tape base material of the other of the folded sections are connected in the width direction via perforations, and that, in the providing of the hook member of the fastening tape, the connected body is placed across the pair of side flap-folded sections, both end sections of the connected body being joined to the side flap-folded sections, respectively, a pair of the hook members being engaged at a position of the flap segment that faces the gap.

According to such a method of manufacturing an absorbent article, the above-mentioned problems of being caught during transportation can be more positively prevented.

With such method of manufacturing an absorbent article, it is preferable that, the absorbent body includes a fluid absorbent fiber as a main material, the continuous body of absorbent main bodies includes a back surface sheet member that continues in the transport direction, the absorbent main bodies being arranged on one face of the back surface sheet member intermittently in the transport direction, and a front surface sheet member that covers the other face of the back surface sheet member and is provided for each of the absorbent bodies, the back surface sheet member includes an unprovided region in which the front surface sheet member is not provided, the unprovided region being situated between the absorbent bodies that are adjacent to each other, and that, in the joining of the flap segment to the continuous body of absorbent main bodies in an overlapped manner, the flap segment is joined to the unprovided region with the flap segment covering each end edge of a pair of front surface sheet members adjacent to the unprovided region.

According to such a method of manufacturing an absorbent article, since the front surface sheet members are intermittently arranged with respect to the back surface sheet member, the total amount of the front surface sheet members can be reduced. Even if the fluid absorbent fiber leaks out from the end edge of the front surface sheet member, the leaked out fluid absorbent fiber will be received and constrained by the flap segment that covers the end edge. Thus, the leaking of the fluid absorbent fiber out of the absorbent main body can be effectively suppressed. That is to say, while effectively keeping the fluid absorbent fiber related to the absorbent body inside the absorbent main body, the amount of the front surface sheet member can be reduced by the amount of the unprovided region. As a result, the manufacturing cost of the absorbent article can be reduced.

With such method of manufacturing an absorbent article, it is preferable that, in the joining of the flap segment to the continuous body of absorbent main bodies in an overlapped manner, the flap segment is provided in such a manner that the flap segment covers a longitudinal end section of the absorbent body, a pocket section that opens toward the end section of the absorbent body being formed on the flap segment by setting a joining region to the continuous body of absorbent main bodies on the flap segment in such a manner that the joining section surrounds the end section of the absorbent body from three directions in a U-shape.

According to such a method of manufacturing an absorbent article, the excretory fluid that flows to the end section in the longitudinal direction along a skin-side surface of the front surface sheet member is received by the pocket section serving as a weir. Therefore, an absorbent article having a high anti-leak property of excretory fluid out of the absorbent article can be manufactured.

Also provided is an apparatus that manufactures an absorbent article including an absorbent main body, a pair of first side flaps and a pair of second side flaps, the absorbent main body having an absorbent body that absorbs fluid, the absorbent main body being placed against the crotch of a wearer, the pair of first side flaps being provided at one end section of the absorbent main body in a longitudinal direction, the first side flaps being folded in an outwardly projectable manner in a width direction of the absorbent main body from respective end edges of the absorbent main body in the width direction, the pair of second side flaps being provided at the other end section of the absorbent main body in the longitudinal direction, the second side flaps being folded in an outwardly projectable manner in the width direction of the absorbent main body from respective end edges of the absorbent main body in the width direction, the apparatus including:

a first device that forms a pair of side flap-folded sections by folding a continuous sheet in such a manner that end sections in a width direction of the continuous sheet are folded inwardly in the width direction, respectively, while the continuous sheet that is a base material of the first side flap and the second side flap is being transported in a continuous direction of the continuous sheet;

a second device that produces a flap segment by segmenting the continuous sheet at a predetermined pitch in the continuous direction, the continuous sheet having the pair of side flap-folded sections formed thereon;

a third device that joins the flap segment to a continuous body of absorbent main bodies in an overlapped manner with the flap segment lying across a border position between the absorbent main bodies adjacent to each other in the transport direction, while the continuous body that includes the absorbent main bodies continuing in the longitudinal direction is being transported in a transport direction that corresponds to a continuous direction of the continuous body; and a fourth device that divides the flap segment into a section having the pair of first side flaps and a section having the pair of second side flaps by segmenting the continuous body of absorbent main bodies at the border position with the flap segment being joined to the continuous body of absorbent main bodies.

With such an apparatus that manufactures an absorbent article, effects similar to those of the above-mentioned manufacturing method can be obtained.

===Present Embodiment===

For example, a disposable diaper 1 is manufactured with a method of manufacturing an absorbent article according to the present embodiment. Accordingly, before explaining this manufacturing method, a structure of the disposable diaper 1 will be described.

<<<Disposable Diaper 1>>>

FIGS. 1A to 1D and FIG. 2 are explanatory diagrams of the disposable diaper 1. FIG. 1A is a plan view in an open state. FIGS. 1B to 1D are cross-sectional views taken along B-B, C-C, and D-D in FIG. 1A, respectively. FIG. 2 is a perspective view of the disposable diaper 1 in a state of being worn.

As shown in FIG. 1A, the diaper 1 includes an absorbent main body 10 that absorbs excretory fluid (corresponds to fluid) and that is placed against the crotch of a wearer and, a stomach-side band member 21 joined to a front end section 10a (corresponds to one end section) of the absorbent main body 10 in a longitudinal direction to cover a stomach side part of a wearer, and a back-side band member 25 joined to a rear end section 10b (corresponds to the other end section) of the absorbent main body 10 in the longitudinal direction to cover a back side part of the wearer. An external appearance of the diaper 1 in the open state is substantially H-shaped in a planar view. In this open state, the longitudinal direction of the diaper 1 coincides with the longitudinal direction of the absorbent main body 10, and the width direction (a direction orthogonal to the longitudinal direction) of the diaper 1 coincides with the width direction of the absorbent main body 10, and thus will be treated in such a manner in the description below. It is to be noted that the width direction will also be referred to as a left-right direction.

From this open state, the diaper 1 is folded in half with a central section C10 of the absorbent main body 10 in the longitudinal direction being a fold position, and, in this folded state, both end sections 25e, 25e of the back-side band member 25 in a width direction are fixed with an appropriate fixing member 30 to the front end section 10a of the absorbent main body 10. Accordingly, a waist opening 1a and a pair of leg openings 1b, 1b shown in FIG. 2 are formed and thus the diaper 1 comes to the state of being worn.

In the present embodiment, a releasable fixing member such as a hook-and-loop type fastener is used as the above-mentioned fixing member 30 and thus this diaper 1 is configured as a so-called open type (spread-out type) diaper. Each of the constituent elements 10, 21 and 25 of the diaper 1 including this fastening member 30 will be described below.

As shown in FIGS. 1A to 1D, the absorbent main body 10 includes an absorbent body 11 made of fluid-absorbing fiber such as pulp fiber, a fluid permeable front surface sheet member 12 that covers the absorbent body 11 from a wearer's skin side, and a fluid impermeable back surface sheet member 13 of, for example, a double layer structure that covers the absorbent body 11 from a non-skin side (a side opposite to the front surface sheet member 12). The front surface sheet member 12 is, for example, a nonwoven fabric. In this example, the front surface sheet member 12 extends from the skin side to the non-skin side at each end section of the absorbent body 11 in the width direction and joined and integrated to the absorbent body 11 by, for example, adhesion, while covering the above-mentioned each end section. On the other hand, as shown in FIG. 1C, the back surface sheet member 13 includes an exterior sheet 14 that forms an exterior and a fluid impermeable anti-leak sheet 15 such as a film attached to the skin side surface of the exterior sheet 14.

The absorbent body 11 in which the above-mentioned front surface sheet member 12 is integrated is joined to the anti-leak sheet 15 on the back surface sheet member 13 by, for example, adhesion, and thus the absorbent main body 10 is formed.

It is to be noted that the absorbent body 11 may contain high-absorbent polymer. Further, a fluid permeable sheet such as tissue paper may be interposed between the front surface sheet member 12 and the absorbent body 11.

Also, in the example shown in FIG. 1C, in order to form a leg-surrounding gathering section at each end section of the back surface sheet member 13 in a width direction, an elastic member 16 such as an elastic yarn is attached to each end section of the exterior sheet 14 in a width direction in an extended state along the longitudinal direction, and the above-mentioned each end section is folded inwardly in the width direction and covers each end section of the elastic member 16 and the anti-leak sheet 15, but it is not limited thereto.

Further, in the example shown in FIG. 1C, in order to form a pair of three-dimensional gathering sections at both end sections of the absorbent main body 10 in the width direction, three-dimensional gathering forming sheets 17, 17 are joined to the end sections of the front surface sheet member 12 in the width direction, respectively, but these sheets 17, 17 can be dispensed with.

The stomach-side band member 21 is a single piece band-like sheet such as a nonwoven fabric elongated in the width direction of the diaper 1, and, as shown in FIGS. 1A and 1B, disposed in such a manner that the front end section 10a of the absorbent main body 10 in the longitudinal direction lies across in its width direction and is joined to the skin-side surface of the front end section 10a with a hot melt adhesive agent or the like. Both end sections 21e, 21e of the stomach-side band member 21 protrude outwardly in the width direction from both end edges of the absorbent main body 10 in the width direction, respectively, and thus a pair of first side flaps 21e, 21e are provided at the left and right of the diaper 1 in the width direction, respectively. It is to be noted that before use of the diaper 1, both first side flaps 21e of the pair of first side flaps 21e are folded inwardly in the width direction of the diaper 1 and, in other words, are not protruded from the both end edges of the absorbent main body 10 (see FIGS. 3A and 3B). Accordingly, in using the diaper 1, as shown in FIGS. 1A and 1B, the first side flaps 21e, 21e are respectively opened outwardly in the width direction of the diaper 1 so as to be protruded from the above-mentioned both end edges.

It is to be noted that the stomach-side band member 21 corresponds to "a section having the pair of first side flaps" in the claims.

The back-side band member 25 is also a single piece band-like sheet such as a nonwoven fabric elongated in the width direction of the diaper 1, and, as shown in FIGS. 1A and 1C, disposed in such a manner that the rear end section 10b of the absorbent main body 10 in the longitudinal direction lies across in its width direction and joined to the skin-side surface of the rear end section 10b with a hot melt adhesive agent or the like. Both end sections 25e, 25e of the back-side band member 25 also protrude outwardly in the width direction from both end edges of the absorbent main body 10 in the width direction, respectively, and thus a pair of second side flaps 25e, 25e is formed in such a manner that the second side flaps 25e are provided at the left and right of the diaper 1 in the width direction, respectively. Similarly to the above-mentioned first side flaps 21e, it is to be noted that before use of the diaper 1, both second side flaps 25e of the pair of second side flaps 25e are folded inwardly in the width direction of the diaper 1 and, in other words, are not protruded from the both end edges of the absorbent main body 10 (see FIGS. 3A and 3C). Accordingly, in using the diaper 1, as shown in FIGS. 1A and 1D, the second side flaps 25e, 25e are also respectively opened outwardly in the width direction of the diaper 1 so as to be protruded from the both end edges. It is to be noted that the back-side band member 25 corresponds to "a section having the pair of second side flaps" in the claims.

As shown in FIGS. 1A, 1B, 1D and 2, the fixing member 30 includes fastening tapes 31, 31 that are respectively provided at tip end sections of the pair of second side flaps 25e, 25e and a target tape 37 made of nonwoven fabric that is provided on a non-skin side surface of the front end section 10a of the absorbent main body 10 so as to releasably engage with the fastening tapes 31, 31.

As shown in FIGS. 1A and 1D, each fastening tape 31 includes a rectangular band-shaped sheet as a tape base material 32 with one end section of the tape base material 32 in a longitudinal direction being fixed to a tip end section of the second side flap 25e and the other end section being protruded outwardly in the width direction from the tip end section of the second side flap 25e. A hook member 33 of a hook-and-loop fastener is secured to this protruding section and in a fixed state shown in FIG. 2, the hook member 33 engages the above-mentioned target tape 37.

Figure 3A:
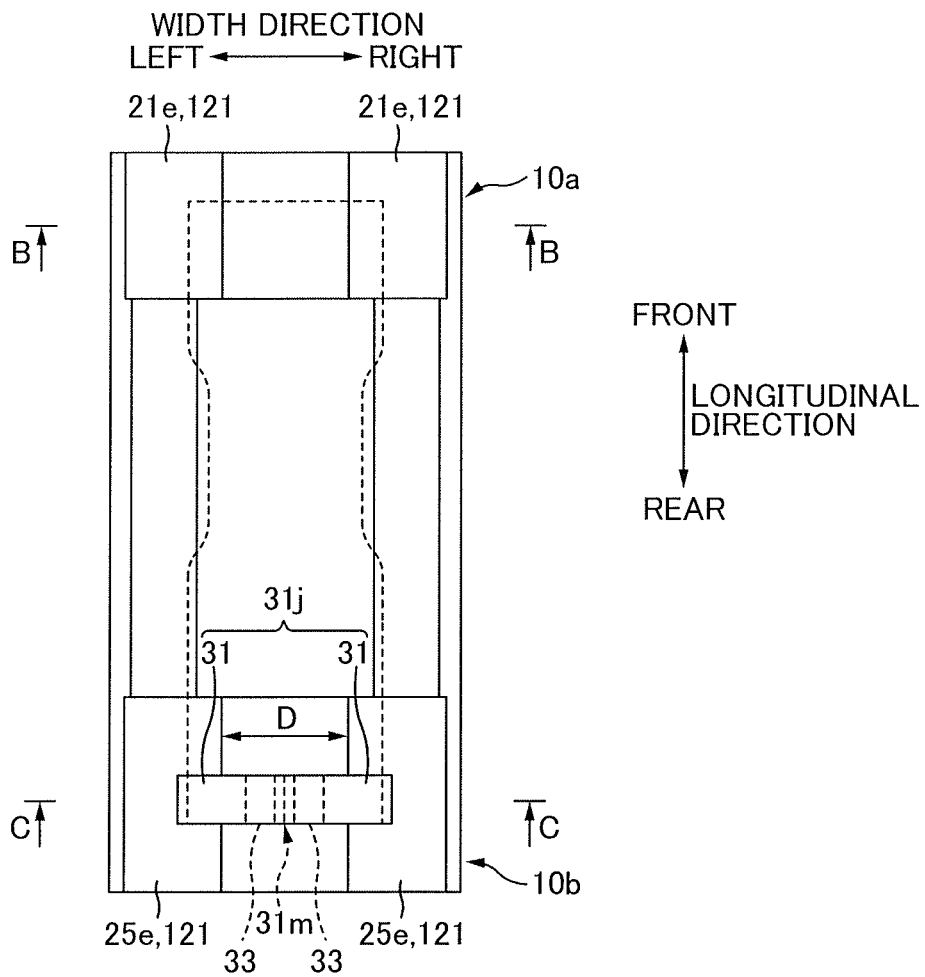
FIG. 3A is a plan view of a disposable diaper 1 in a state where first and second side flaps 21e and 25e are folded.
Figure 3B:
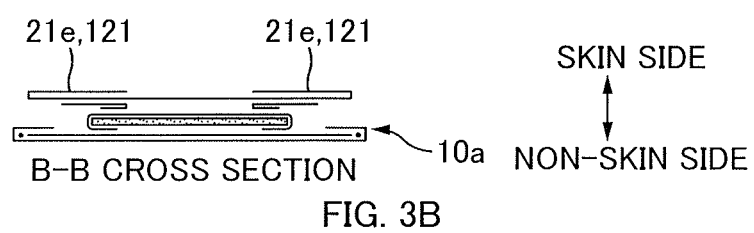
FIGS. 3B and 3C are cross sectional views taken along B-B and C-C in FIG. 3A, respectively.
Figure 3C:
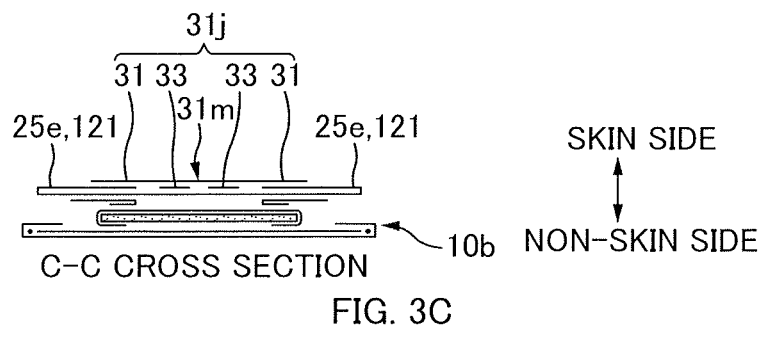

FIGS. 3A to 3C are explanatory diagrams of the fastening tape 31 before use. FIG. 3A is a plan view of the disposable diaper 1 before use and FIGS. 3B and 3C are cross sectional views taken along B-B and C-C in FIG. 3A, respectively.

As has been described above, before use of the diaper 1, the second side flaps 25e, 25e are each folded inwardly in the width direction of the diaper 1 (see FIGS. 3A to 3C) and, accordingly, the tip end portions of pair of second side flaps 25e, 25e are directed inwardly in the width direction of the diaper 1 and are arranged at the left and right in the width direction with a distance D between each other. On the other hand, at this point, the above-mentioned fastening tapes 31 as a pair are still a single member connected (linked) to each other via perforations 31m and such a connected body 31j of fastening tapes 31 is provided across and joined to folded sections 121, 121 that are tip end sections of the pair of side flaps 25e, 25e.

Accordingly, in using the diaper 1, firstly, the above-mentioned connected body 31j is divided into a pair of fastening tapes 31 by separation at the perforations 31m. Thereafter, each fastening tape 31 is opened outwardly in the width direction together with the second side flap 25e and thus each fastening tape 31 comes to a fixable state in which it is protruded outwardly in the width direction of the diaper 1 as shown in FIGS. 1A and 1D.

In putting the diaper 1 on the wearer, the fastening tapes 31, 31 are, as shown in FIG. 2, fixed by engaging with the target tape 37 while pulling the diaper 1 towards left and right in the width direction of the diaper 1 with the pair of second side flaps 25e, 25e or with the pair of fastening tapes 31, 31. Here, these second side flaps 25e, 25e are both apart of the back-side band member 25 or, in other words, both second side flaps 25e, 25e of the pair of second side flaps 25e, 25e belong to the same nonwoven fabric that continues in the width direction. Therefore, a tensile force in the width direction acting on the diaper 1 at the time of putting it on can be effectively counteracted by a tensile strength in the width direction of the back-side band member 25 itself that is the same nonwoven fabric. As a result, the diaper 1 can be quickly put on without unintentional splitting or the like.

Figure 4A:
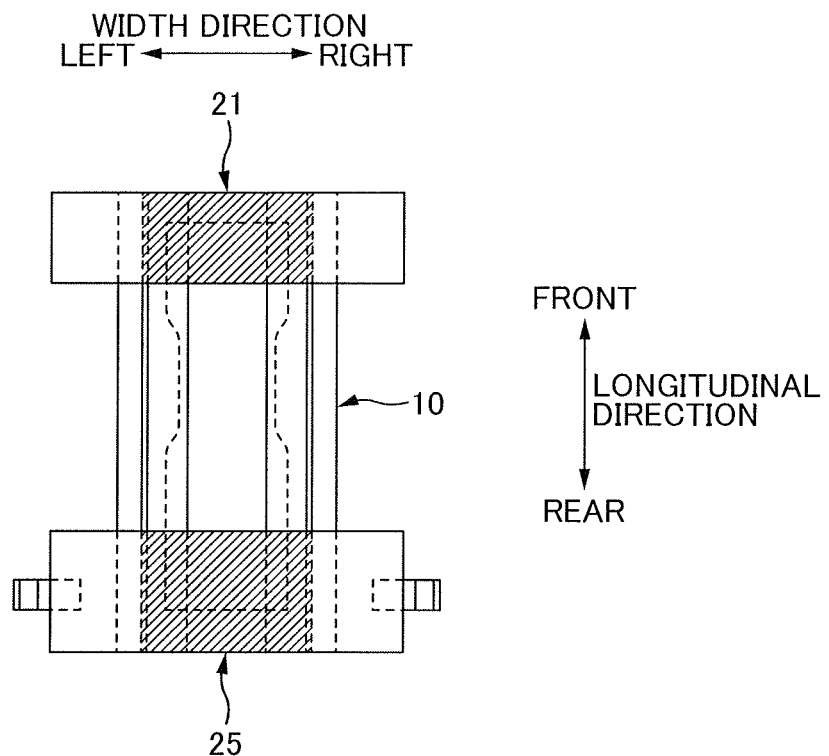
FIGS. 4A and 4B are explanatory diagrams of a joining region that joins a stomach-side band member 21 and a backside band member 25 to an absorbent main body 10, respectively.
Figure 4B:
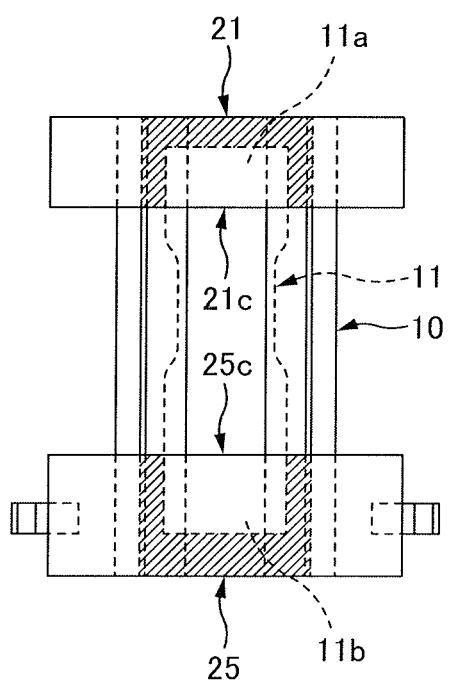

Further, the back-side band member 25 having these second side flaps 25e, 25e as a part thereof is arranged in such a manner that the absorbent main body 10 lies across its width direction, and thus a joining region with the absorbent main body 10 can be kept large across an entire region in the width direction (e.g., see hatched regions in FIGS. 4A and 4B). Accordingly, a joining strength between the absorbent main body 10 and the back-side band member 25 can be made high and as a result, a high durability can be obtained.

A joining region in which the stomach-side band member 21 and the back-side band member 25 are joined to the absorbent main body 10 may be, as shown by hatchings in FIG. 4A, a joining region that is substantially the entire region in which the stomach-side band member 21 and the back-side band member 25 overlap and may be a joining region that is substantially the entire region in which the back-side band member 25 and the absorbent main body 10 overlap. However, the following elaboration may also be made.

FIG. 4B is a plan view of the open state in which the joining region is shown by hatchings. As shown in 4B, the stomach-side band member 21 and the back-side band member 25 are arranged to cover the end sections 11a, 11b, respectively, of the absorbent body 11 in the longitudinal direction from the skin side, and joining regions to the absorbent main body 10 (see hatched regions in FIG. 4B) are provided in such a manner that they surround the corresponding end sections 11a, 11b of the absorbent body 11 from three directions in a U-shape. Accordingly, a central section 21c of the stomach-side band member 21 in the width direction and a central section 25c of the back-side band member 25 in the width direction are configured so as to be capable of contacting and separating from the absorbent main body 10, and, in other words, these central sections 21c and 25c serve as pocket sections that have openings towards corresponding end sections 11a and 11b of the absorbent body 11, respectively. Therefore, these pocket sections serve as weirs for excretory fluid that may flow out along the longitudinal direction of the diaper 1 on the skin-side surface of the front surface sheet member 12 and effectively receive this. In other words, the diaper 1 has a high anti-leak property against excretory fluid.

<<<Method of Manufacturing a Disposable Diaper 1>>>

Figure 5:
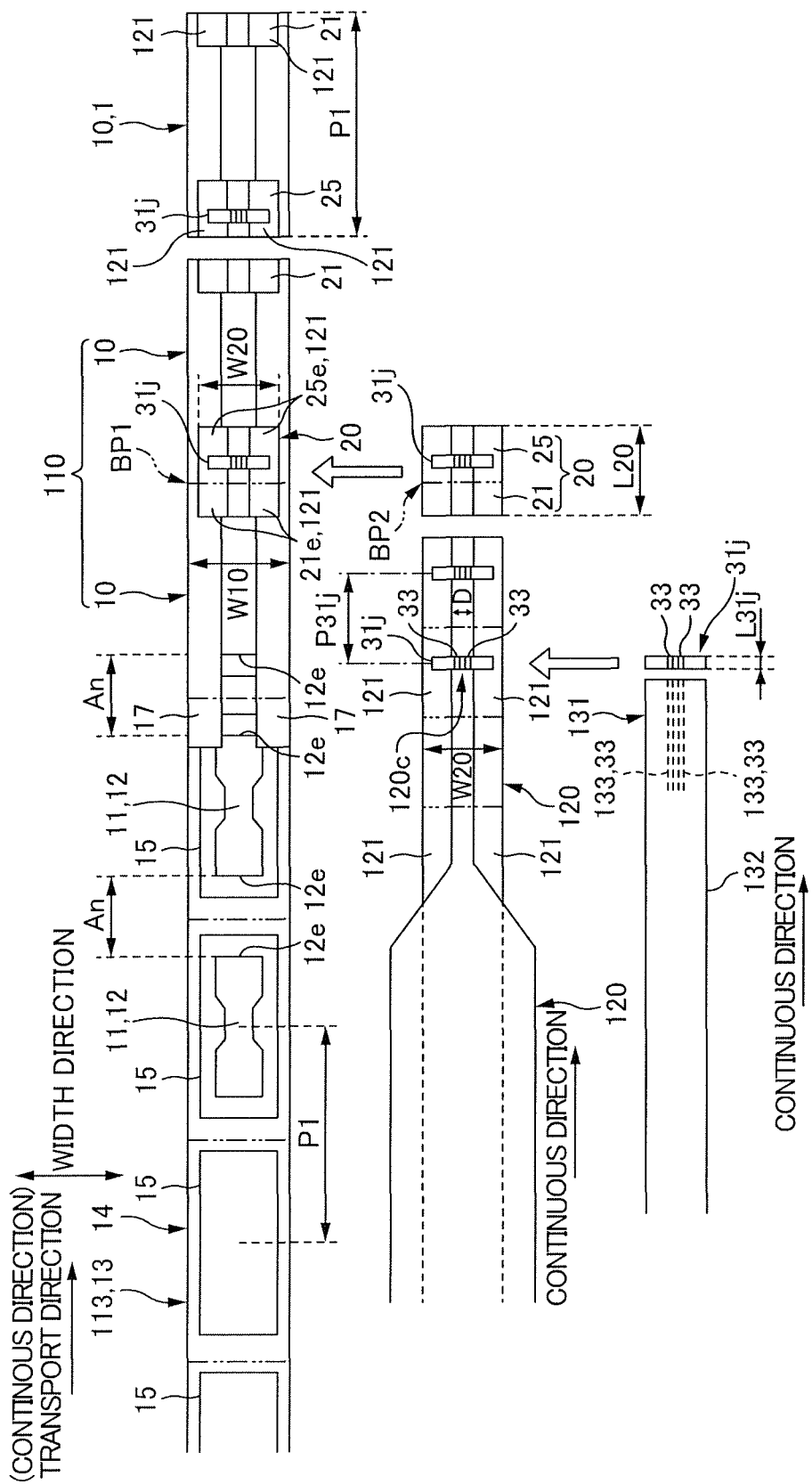
FIG. 5 is an explanatory diagram of a method of manufacturing the disposable diaper 1 of the present embodiment.

FIG. 5 is an explanatory diagram of a method of manufacturing the diaper 1. The diaper 1 is manufactured with a so-called "longitudinal flow process". In this longitudinal flow process, with the longitudinal direction of the diaper 1 being aligned with a transport direction, semi-products of the diapers 1 are transported at a predetermined pitch P1 in the transport direction, and, the diaper 1 is manufactured by sequentially performing, such as, joining and processing of the components of the diaper 1 for each of the semi-products. Here, since the longitudinal direction of the diaper 1 generally coincides with the longitudinal direction of the absorbent main body 10 as shown in FIG. 1A, the above-mentioned "longitudinal flow process" may also be referred to as follows. That is to say, the longitudinal flow process may also be referred to as "a method of manufacturing the diaper 1 by performing, such as, joining and processing of the components of the diaper 1 on the continuous body 110 of the absorbent main bodies 10 while a plurality of absorbent main bodies 10 are, in a state of a continuous body 110 continuing in a longitudinal direction thereof, transported with its continuous direction being the transport direction."

The manufacturing method of the present embodiment includes steps (1) to (4) described below in such a longitudinal flow process, and the above-mentioned diaper 1 is completed after these steps (1) to (4).

(1) Producing and transporting step of the continuous body 110 of absorbent main bodies 10 in which the continuous body 110 of absorbent main bodies 10 is produced and continuously transported.

(2) Producing step of a continuous body 131 of connected bodies of fastening tapes 31.

(3) Producing and joining step of a band member intermediate part 20 in which a band member intermediate parts 20 (corresponds to "flap segmentation piece") in a state before being divided into the stomach-side band member 21 and the back-side band member 25 is produced, and the band member intermediate part 20 is joined to the continuous body 110 of absorbent main bodies 10.

(4) Dividing step of dividing the band member intermediate part 20 into the stomach-side band member 21 and the back-side band member 25 in which the continuous body 110 of absorbent main bodies 10 whereto the band member intermediate part 20 is joined is segmented at a product pitch P1 of the diaper 1.

Hereinafter, each of the steps (1) to (4) will be described.

(1) Producing and Transporting Step of Continuous Body 110 of Absorbent Main Bodies 10

In this step, the continuous body 110 of absorbent main bodies 10 in which a plurality of absorbent main bodies 10 are continuing in the longitudinal direction thereof is produced and the produced continuous body 110 of absorbent main bodies 10 is transported with its continuous direction being a transport direction.

In detail, first, as shown in FIG. 5 at a top part, a continuous body 113 of the back surface sheet member 13 is transported with its continuous direction being a transport direction by a suction conveyor (vacuum conveyor) that is not shown. At this time, the exterior sheet 14 related to the back surface sheet member 13 is a sheet that is continuous in the transport direction, whereas, the anti-leak sheet 15 in a cut sheet state that are intermittently disposed on the exterior sheet 14 at product pitch P1. Also, at the same time, the elastic member 16 such as an elastic yarn has already been disposed and secured in an extended state along the continuous direction at each of the end sections in the width direction of the exterior sheet 14, and each of the end sections is folded over inwardly in the width direction. In FIG. 5, in order to avoid confusion of the drawings, the above-mentioned elastic member 16 and the folding of the exterior sheet 14, etc., are not illustrated.

Next, the absorbent body 11 is placed and joined in correspondence with each anti-leak sheet 15. It is to be noted that, the absorbent body 11 at the time of placing is in a state where the skin-side surface thereof and each of the end sections in the width direction are covered with the above-mentioned front surface sheet member 12.

The placing and joining process of such absorbent body 11 to the continuous body 113 of back surface sheet members 13 is, for example, performed by a transfer device (not shown). The transfer device is arranged on a transport path of the continuous body 13 of back surface sheet members 13 and includes a rotation drum that rotates in a circumferential direction. A plurality of suction sections are provided on an outer peripheral surface of the rotation drum, and, at each suction section, the absorbent body 11 whereto the front surface sheet member 12 is integrated is held by suction. With the rotation of the rotation drum, as the absorbent body 11 passes the transport path of the back surface sheet member 13, the absorbent body 11 is transferred to the back surface sheet member 13. By the time of this point of transfer, a hot melt adhesive is applied to at least one of the absorbent body 11 and the back surface sheet member 13. Therefore, with the transferring described above, the absorbent body 11 is jointed to the back surface sheet member 13.

With such intermittent arrangement of the absorbent bodies 11 as described above, an unprovided region An in which the front surface sheet member 12 is not provided is formed on the continuous body 113 of back surface sheet members 13 between absorbent bodies 11 and 11 that are adjacent to each other in the transport direction, and with the formation of such unprovided region An, an amount of material of the front surface sheet member 12 can be reduced.

Finally, a three-dimensional gathering section is formed at each of the end sections of the continuous body 110 of the absorbent main body 10 in the width direction. That is to say, three-dimensional gathering forming sheets 17, 17 are continuously supplied and joined to the left and right, respectively, in the width direction so as to cover respective end sections of the continuous body 113 of back surface sheet members 13 in the width direction and respective end sections of the front surface sheet member 12 in the width direction from the above (skin side) during the transportation.

(2) Producing Step of Continuous Body 131 of Connected Bodies 31j of Fastening Tapes 31

As shown in FIG. 5 at a bottom part, a production line related to this process is a system that is separate from the above-mentioned "Producing and Transporting Step of Continuous Body 110 of Absorbent Main Bodies 10". In this step, the continuous body 131 of connected bodies 31j of fastening tapes 31 is produced. The continuous body 131 of connected bodies 31j of fastening tapes 31 includes the connected bodies 31j of fastening tapes 31 shown in FIG. 3A continuing in a lateral direction (a direction orthogonal to the longitudinal direction of the connected body 31j) of the connected bodies 31j. In other words, the connected body 31j of fastening tapes 31 shown in FIG. 3A described above can be obtained by dividing the continuous body 131 shown in FIG. 5 at a predetermined pitch L31j in a continuous direction thereof.

Such continuous body 131 of connected bodies 31j of fastening tapes 31 is produced in the following manner. First, as shown in FIG. 5 at the bottom part, a continuous sheet 132 whose width is double the length in the longitudinal direction of the tape base material 32 and that serves as as an original fabric of the tape base material 32 of the fastening tape 31 is unreeled from a reel device or the like and transported in its continuous direction. Also, continuous bodies 133 and 133 of a hook member 33 of a pair of hook-and-loop fasteners are unreeled from respective reel devices and are transported in their continuous directions. Then, with the continuous direction of the continuous sheet 132 being aligned in parallel with the continuous directions of the continuous bodies 133 and 133 of the hook member of the pair of hook-and-loop fasteners, the continuous bodies 133 and 133 of the hook member 33 of the pair of hook-and-loop fasteners are arranged and aligned in the width direction on a central section of the continuous sheet 132 in the width direction and these continuous bodies 133 and 133 are joined to the central section by adhesion, welding or the like. Then, perforations 31m (not shown in FIG. 5) are formed at a portion between the hook members 33 and 33 of the hook-and-loop fastner on the continuous sheet 132 and thus the continuous body 131 of connected bodies 31j of fastening tapes 31 is produced.

(3) Producing and Joining Step of Band Member Intermediate Part 20

As shown in FIG. 5 at a middle part, a production line related to this step is a system that is separate from the above-mentioned "Producing and Transporting Step of Continuous Body 110 of Absorbent Main Bodies 10" and "Producing Step of Continuous Body 131 of Connected Bodies 31j of Fastening Tapes 31".

In this step, the band member intermediate part 20 which is in a state before being divided into the stomach-side band member 21 and the back-side band member 25, and the band member intermediate part 20 is joined to the continuous body 110 of absorbent main bodies 10 that has been produced in the above-mentioned "Producing and Transporting Step of Continuous Body 110 of Absorbent Main Bodies 10" and that is being transported.

In detail, first, as an original fabric of the band member intermediate part 20, the continuous sheet 120 of such as a nonwoven fabric is continuously unreeled from the reel device. Then, while the unreeled continuous sheet 120 is being transported in its continuous direction, each of the end sections of the continuous sheet 120 in the width direction is folded inwardly in the width direction, respectively, and thus a pair of folded sections 121, 121 is formed. These folded sections 121, 121 will later become the above-mentioned first side flaps 21e, 21e and second side flaps 25e, 25e. Hereinafter, this folded section 121 will also be referred to as a side flap-folded section 121.

Figure 6:
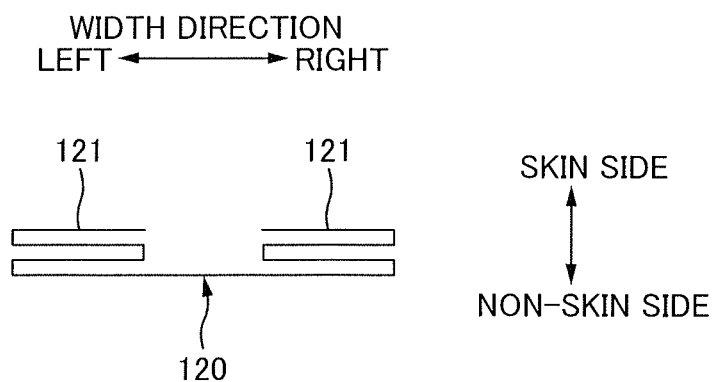
FIG. 6 is an explanatory diagram of a variant of a manner in which a side flap-folded section 121 is folded.

Here, the folding may be a V-shaped fold with only one fold as shown in an example of FIG. 5 (i.e., examples of FIG. 3B and 3C) or may be an M-shaped fold with three folds, which is an example of a plurality of (an odd number of) folds, shown in a cross sectional view of FIG. 6. However, as shown in FIG. 5, in a contracted width state in which the side flap-folded sections 121, 121 are folded, it is preferable that a width W20 of the continuous sheet 120 is smaller than a width W10 of the continuous body 110 of the absorbent main bodies 10, and in this example, it is configured in such a manner. Its effect will be described later.

A folding process of each of the end sections of the continuous sheet 120 is continuously performed by, for example, a continuous folding plate device (corresponds to a first device) not shown. The continuous folding plate device is arranged on the transport path of the continuous sheet 120. The continuous folding plate device includes a guide plate that gradually guides each of the end sections inwardly in the width direction along with the transportation of the continuous sheet 120 so as to fold each of the end sections.

Next, as shown in FIG. 5 at the bottom part, the continuous body 131 of connected bodies 31j of fastening tapes 31 that is continuously supplied from the above-mentioned production line is segmented at the predetermined pitch L31j in the continuous direction thereof, and thus the connected bodies 31j of fastening tapes are is produced. Then, the connected body 31j of fastening tapes 31 is supplied at a predetermined supply pitch P31j in the continuous direction of the continuous sheet 120, and, as shown in FIG. 5 in the middle part, both end sections of the connected body 31j of fastening tapes 31 are, while being disposed across tip end sections of the side flap-folded sections 121, 121 that are directed inwardly in the width direction of the continuous sheet 120, joined to the tip end sections, respectively, with a hot melt adhesive and the like.

It is to be noted that, at this time, the leading end sections of respective side flap-folded sections 121, 121 are in a state where there is a distance D is between each other. Also, the hook members 33, 33 of the pair of hook-and-loop fasteners provided at the central section of the connected body 31j of fastening tapes 31 are placed in this distance D, and thus, the hook members 33, 33 of the pair of hook-and-loop fastener opposes the the central section 210c of the continuous sheet 120 via the distance D. Therefore, the hook members 33, 33 of the hook-and-loop fastener engage the central section 210c of the continuous sheet 120, and thus, during the subsequent transportation, the side flap-folded sections 121, 121 will not open unnecessarily. In other words, the side flap-folded sections 121, 121 will be positively kept in a folded state.

The supply pitch P31j of the connected body 31j of above-mentioned fastening tapes 31 is set at the same value as a length L20 of the band member intermediate part 20 of the diaper 1 in the longitudinal direction and, further, the connected body 31j of fastening tapes 31 is arranged and joined to a portion corresponding to the back-side band member 25 on the continuous sheet 120.

Figure 7:
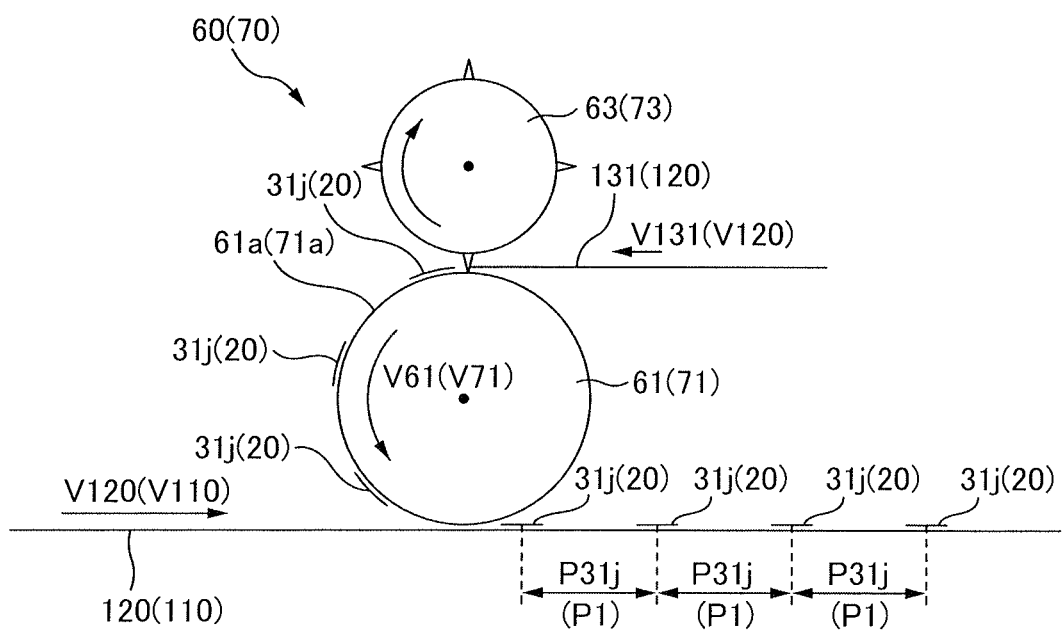
FIG. 7 is a schematic side view of a transfer apparatus 60 (70).

Such intermittent supplying and joining process of the connected body 31j to the above-mentioned continuous sheet 120 is, for example, performed by the transfer device 60. FIG. 7 is a schematic side view of the transfer device 60.

The transfer device 60 includes a rotation drum 61 that rotates at a circumferential speed V61 that is substantially the same as a transport speed V120 of the continuous sheet 120, and a suction section that is capable of attaching and detaching the connected body 31j of fastening tapes 31 is provided on an outer circumferential surface 61a of the rotation drum 61. Further, a cutter roll 63 is arranged so as to oppose to the outer circumferential surface 61a.

Then, the continuous body 131 of connected bodies 31j of fastening tapes 31 is forwarded into a gap between the rotation drum 61 and the cutter roll 63 at a supply speed V1 that is slower than the circumstantial speed V61 of the rotation drum 61. Accordingly, the continuous body 131 is basically forwarded while relatively sliding in a direction delaying with respect to the outer circumferential surface 61a of the rotation drum 61, and at the time the continuous body 131 has been forwarded by an amount corresponding to a size L31j in a lateral direction of the connected body 31j of fastening tapes 31, the tip end section of the connected body 131 is segmented by the cutter roll 63. Then, the segmented tip end section is, as the connected body 31j of fastening tapes 31, held on the outer circumferential surface 61a of the rotation drum 61 by suction, rotated in an integrated manner with the rotation drum 61, intermittently forwarded towards the above-mentioned continuous sheet 120 that is transported in a state of opposing the outer circumferential surface 61a of the rotation drum 61, and joined to the same continuous sheet 120 at the above-mentioned supply pitch P31j.

Then, as shown in FIG. 5 in the middle part, the continuous sheet 120 whereto the connected body 31j of fastening tapes 31 is joined is segmented in its continuous direction at the same pitch as the above-mentioned supply pitch P31j (i.e., the above-mentioned length L20 of the band member intermediate part 20) and thus the above-mentioned band member intermediate part 20 is produced that is a continuation of the stomach-side band member 21 and the back-side band member 25. Then, as shown in FIG. 5 at the top part, the band member intermediate part 20 is joined to the continuous body 110 of absorbent main bodies 10 by a hot melt adhesive and the like. At the time of joining, each band member intermediate part 20 is positioned so as to be provided across a border position BP1 between the absorbent main bodies 10 and 10 that are adjacent to each other in the transport direction. In detail, the band member intermediate part 20 is placed over and joined to the continuous body 110 of absorbent main bodies 10 in such a manner that the border position BP1 between the absorbent main bodies 10 coincides with a border position BP2 between the stomach-side band member 21 and the back-side band member 25. Thus, in a subsequent "dividing process", by segmenting the continuous body 110 of absorbent main bodies 10 at the product pitch P1, the band member intermediate part 20 will also be divided along the width direction together with the continuous body 110 of absorbent main bodies 10 and, accordingly, the band member intermediate part 20 will be divided into the stomach-side band member 21 and the back-side band member 25.

As has been described above, since the front surface sheet member 12 is integrated with the absorbent body 11, the front surface sheet members 12 are intermittently arranged in the transport direction on the continuous body 110 of absorbent main bodies 10 in a manner similar to the absorbent body 11. Accordingly, as shown in FIG. 5 at a top part, the unprovided region An of the front surface sheet member 12 is formed between the front surface sheet members 12 and 12 that are adjacent to each other in the transport direction and that are forming a pair. Therefore, a pulp fiber or a high-absorption polymer of the absorbent main body 10 may leak out from an end edge 12e of the front surface sheet member 12 in the transport direction. In order to avoid this, in the joining of the above-mentioned band member intermediate part 20 to the continuous body 110 of absorbent main bodies 10, the band member intermediate part 20 is arranged in such a manner that the band member intermediate part 20 covers each of the end edges 12e, 12e of a pair of front surface sheet member 12 that are adjacent to the unprovided region An on the continuous body 110. Thus, even if pulp fiber or the like leaks from the end edge 12e of the front surface sheet member 12, the pulp fiber and the like that has leaked will be received and confined by the band member intermediate part 20 (the stomach-side band member 21 and the back-side band member 25 in a state of product of the diaper 1) and thus the pulp fiber and the like is effectively suppressed from being leaking out of the diaper 1.

Such processes of producing the band member intermediate parts 20 by segmentation and intermittent supplying and joining of the band member intermediate parts 20 to the continuous body 110 of absorbent main bodies 10 is performed, for example, by a transfer device 70 (corresponds to the second and third devices) that has a configuration similar to that of the transfer device 60 that has been already described with reference to FIG. 7. That is to say, as shown in FIG. 7, the transfer device 70 includes a rotation drum 71 that rotates at a circumferential speed V71 that is substantially the same as a transport speed V110 of the continuous body 110 of absorbent main bodyies 10, and a suction section that is capable of attaching and detaching the band member intermediate part 20 is provided on an outer circumferential surface 71a of the rotation drum 71. Further, a cutter roll 73 is arranged so as to oppose the outer circumferential surface 71a.

Then, the continuous sheet 120 related to the band member intermediate part 20 is forwarded into a gap between the rotation drum 71 and the cutter roll 73 at a supply speed V120 that is slower than the circumstantial speed V71 of the rotation drum 71. Accordingly, the continuous sheet 120 is basically forwarded while relatively sliding in a direction delaying with respect to the outer circumferential surface 71a of the rotation drum 71, and at the time the continuous sheet 120 has been forwarded by an amount corresponding to the length L20 of the band member intermediate part 20, the tip end section of the continuous sheet 120 is segmented by the cutter roll 73. Then, the segmented tip end section is, as the band member intermediate part 20, held by suction on the outer circumferential surface 71a of the rotation drum 71, rotated in an integrated manner with the rotation drum 71, intermittently forwarded towards the continuous body 110 of absorbent main bodies 10 that is transported in a manner opposing the outer circumferential surface 71a of the rotation drum 71, and joined to the same continuous body 110 at the above-mentioned product pitch P1.

Further, in the present embodiment, as has been described above, both end sections 21e (25e) and 21e (25e) of the band member intermediate part 20 in the width direction are folded inwardly in the with direction based on the side flap-folded sections 121, and, as has been described above, the width W20 of the band member intermediate part 20 in a folded state is narrower than the width W10 of the continuous body 110 of absorbent main bodies 10 (see FIG. 5, top part). Therefore, in the present embodiment, an amount of the band member intermediate part 20 that protrudes outwardly in the width direction from the continuous body 110 of absorbent main bodies 10 is completely eliminated, and thus, while transporting along the transport direction of the continuous body 110 of absorbent main bodies 10 whereto the band member intermediate part 20 is joined, any troubles such the both end sections 21e (25e) and 21e (25e) of the band member intermediate part 20 being caught by various devices in the vicinity of the transport path can be effectively prevented.

Also, as has been described above, since the total width W20 of the band member intermediate part 20 after being folded is narrower than the total width W10 of the continuous body 110 of absorbent main bodies 10, even if the joining position of the band member intermediate part 20 to the absorbent main body 10 becomes somewhat offset from a target position in the width direction, it will be difficult for the band member intermediate part 20 to project outwardly from the both end edges of the continuous body 110 of absorbent main bodies 10 in the width direction. Therefore, in a case where an amount of meandering of the continuous body 110 of absorbent main bodies 10 after the joining of the band member intermediate part 20 is detected based on a position of the above-mentioned end edge of the continuous body 110 of absorbent main bodies 10, false detection can be effectively suppressed.

Further, as has been described above, the pair of side flap fold sections 121 and 121 of the band member intermediate part 20 is constrained by the connected body 31j of fastening tapes 31 to prevent from opening, and, in other words, maintained in a folded state. Therefore, during transportation after the joining of band member intermediate part 20 to the continuous body 110 of absorbent main bodies 10, the side flap-folded sections 121 and 121 can be positively prevented from fluttering.

It is to be noted that, in order to maintain the above-mentioned folded state more positively, further, surfaces that overlap with each other in an opposed manner at the side flap-folded section 121 may be temporarily joined. Here, "to temporarily join" means to join based on the assumption that the surfaces are thereafter used after being separated from each other. In other words, it means to join at such a degree that they are easily separable without loosing their function as the side flaps 21e, 25e in a later use. An example of the joining strength is 0.1 to 0.4 N/25 mm, and preferably, 0.2 N/25 mm.

Such temporary joining process is performed by using an embossed roll and a smooth roll that are arranged with their outer peripheral surfaces opposing each other. A plurality of island-like emboss protrusions are provided on the outer peripheral surface of the emboss roll. While the emboss roll and the smooth roll are rotating respectively, the continuous sheet 120 is passed through the gap between these rolls and the side flap-folded sections 121 are be locally pinched and pressed between the emboss protrusions of the emboss roll and the smooth outer peripheral surface of the smooth roll.

Thus, the pinched and pressed sections are compression bonded, welded and the like and the side flap-folded sections 121 are temporarily joined.

The process timing of the temporary joining is preferably while being the continuous sheet 120 and before being divided into the band member intermediate parts 20. This is because, in the state of separate sheets after being segmented into band member intermediate parts 20, it is difficult to guide the band member intermediate part 20 to the gap between the emboss roll and the smooth roll. More preferably, the temporary joining process is performed before joining the connected body 31j of fastening tapes 31 to the continuous sheet 120. In this manner, it also becomes easier to join the connected body 31j of fastening tapes 31 to the side flap fold section 131.

In a case where this temporary joining is performed, it is not necessary to constrain the folded state by the connected body 31j of fastening tapes 31.

(4) Dividing Step

As shown in FIG. 5 at the top part, in this step, while the continuous body 110 of absorbent main bodies 10 whereto the above-mentioned band member intermediate part 20 is joined is being transported in the transport direction, the continuous body 110 of absorbent main bodies 10 is segmented at the product pitch P1 of the diaper 1 and thus the diaper 1 is completed. As has been described above, with this segmentation, the band member intermediate part 20 is also divided into the stomach-side band member 21 and the back-side band member 25. At this time, the back-side band member 25 is attached to a preceding absorbent main body 10 and the stomach-side band member 21 is attached to a subsequent absorbent main body 10. Such segmentation process is, for example, performed by a cutter roll (corresponds to a fourth device) that is not shown and provided at a predetermined position on the transport path of the continuous body 110 of absorbent main bodies 10.

Due to the segmentation at the above-mentioned product pitch P1, the band member intermediate part 20 will also be divided into the stomach-side band member 21 and the band member intermediate part 20 as has been described above. In this divided state, the side flap-folded section 121 of the back-side band member 25 is constrained by the connected body 31j of fastening tapes 31 so as not to open, and, as for the side flap-folded section 121 of the stomach-side band member 21, since there is no connected body 31j of fastening tapes 31, constraint by the same connected body 31j cannot be expected.

Accordingly, it is preferable to perform the temporary joining process of the above-mentioned side flap-folded sections 121 to at least a portion corresponding to the side flap-folded sections 121 of the stomach-side band member 21 at the band member intermediate part 20. Then, after segmenting at the above-mentioned product pitch P1, in a case where there is a step of transporting the diaper 1 along its longitudinal direction, any problem that may be caused by the fluttering of the side flap fold sections 121 of the stomach-side band member 21 can be prevented in advance.

===Other Embodiments===

Although the embodiments of the present invention have been described above, the present invention is not limited to such embodiments and the following variants are also possible.

Figure 8A:
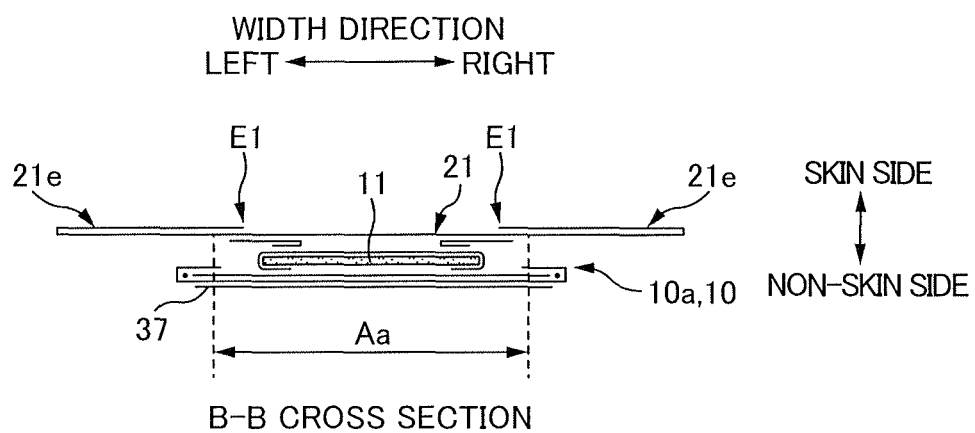
FIGS. 8A and 8B are explanatory diagrams of the first and second side flaps 21e, 25e provided as a double layer structure.
Figure 8B:
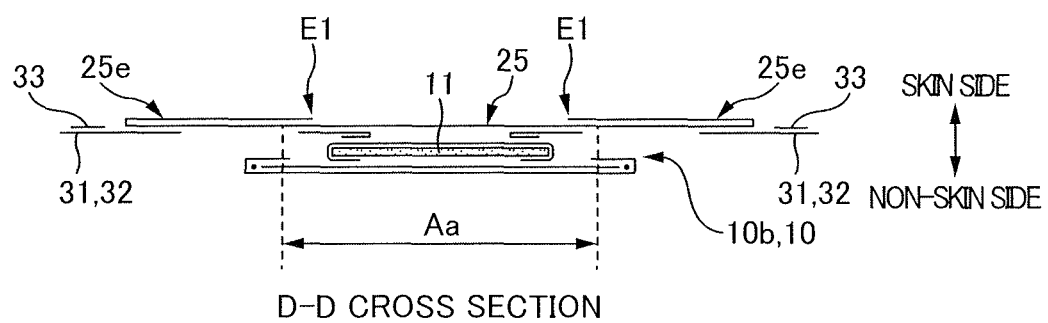

In the above-mentioned embodiments, as shown in FIGS. 1B and 1D, the first side flaps 21e, 21e and the second side flaps 25e, 25e are made of a single layer made of a single nonwoven fabric, but it is not limited thereto. For example, thickness may be made thicker with a plurality of layers provided by folding the end sections 21e, 25e inwardly in the width direction and securing in the folded state. FIGS. 8A and 8B are explanatory diagrams of such an example. It is to be noted that FIGS. 8A and 8B correspond to the B-B cross section and D-D cross section in FIG. 1A, respectively. In this example, the end section 21e of the stomach-side band member 21 and the end section 25e of the back-side band member 25 are each folded once and the end sections 21e, 25e are secured as a double layer. In this manner, stress on the skin of the wearer can be reduced since it is possible to mitigate a tight contact to the skin of the wearer that could occur in a case where the thicknesses of the first side flap 21e and the second side flap 25e are thin. Also, due to the folding, since cut planes that may remain at the end edges of the side flaps 21e, 25e will not come into direct contact with the skin of the wearer, the stress on the skin can be further reduced.

Also, in above-mentioned folding for providing a double layer, it is preferable that each of end edges E1, E1 of the second side flap 25e in the width direction before folding is secured in such a manner that each of the end edges E1, E1 is placed inwardly in the width direction to a joining region Aa of the absorbent main body 10 and the back-side bandmember 25 after folding as shown in FIG. 8B. In this manner, basically, a portion of the second side flap 25e that is not joined to the absorbent main body 10 entirely has a double layer structure and, in other words, a portion of the second side flap 25e that is made of only a single layer of material can be eliminated. As a result, the strength of the second side flap 25e can be improved. Also, in some cases, the basis weight of the back-side band member 25 can be reduced in correspondence with such improvement in the strength, and in such a case, the cost can be reduced. This is similarly applicable to the first side flap 21e in FIG. 8A.

It is to be noted that a folding process for making the first side flap 21e and the second side flap 25e into multilayer is, for example, performed in the above-mentioned "Process of Producing and Joining the Band Member Intermediate Part 20" before forming the side flap fold section 121 by, for example, a continuous fold plate device, and after having folded both end sections of the continuous sheet 120 respectively, the folded state will be secured by processes such as adhesion and welding.

Figure 9:
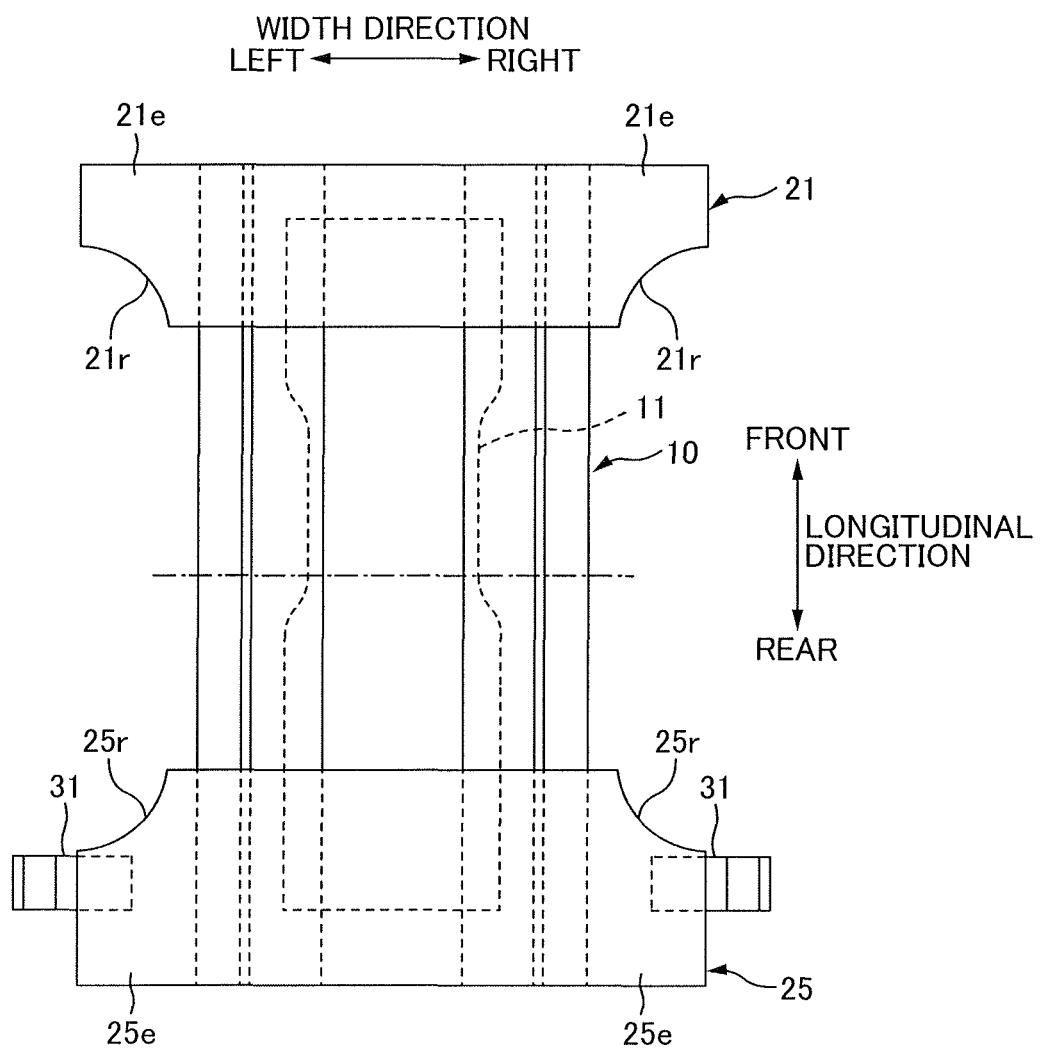
FIG. 9 is an explanatory diagram in a case where the first and second side flaps 21e, 25e have arcuate cut-away sections 21r, 25r.

In the embodiment described above, as shown in FIG. 1A, either of the first and second side flaps 21e, 25e is formed in a substantially rectangular shape, but it is not limited thereto. For example, in order to improve a snug fit property to the legs of the wearer, portions that becomes the leg openings 1b and 1b in FIG. 2 of the first and second side flaps 21e and 25e can be cut away in an arcuate manner as shown in FIG. 9. A round cut process to form such arcuate cut away sections 21r and 25r is performed, for example, in the above-mentioned "Process of Producing and Joining the Band Member Intermediate Part 20", before folding the end sections in the width direction of the continuous sheet 120.

LIST OF REFERENCE NUMERALS 1 disposable diaper (absorbent article), 1a waist opening, 1b leg opening,
10 absorbent main body, 10a front end section (one end section),
10b rear end section (other end section),
11 absorbent body, 11a end section, 11b end section,
12 front surface sheet member, 12e end edge,
13 back surface sheet member, 14 exterior sheet, 15 anti-leak sheet, 16 elastic member, 17 three-dimensional gathering forming sheet,
20 band member intermediate part (flap segment),
21 stomach-side band member (section having a pair of first side flaps),
21c central section, 21e first side flap, 21r arcuate cutout section,
25 back-side band member (section having a pair of second side flaps),
25c central section, 25e second side flap, 30 fixing member,
31 fastening tape, 31j connected body of fastening tapes,
31m perforations, 32 tape base material,
33 hook member of hook-and-loop fastener,
37 target tape, 60 transfer device, 61 rotation drum,
61a peripheral surface, 63 cutter roll,
70 transfer device (second device, third device),
71 rotation drum, 71a peripheral surface, 73 cutter roll,
110 continuous body of absorbent main bodies,
113 continuous body of back surface sheet members,
120 continuous sheet related to band member intermediate parts,
120c central portion,
121 side flap-folded section,
131 continuous body of connected bodies of fastening tapes,
132 continuous sheet related to tape base material,
133 continuous body of hook members of hook-and-loop fastener,
An unprovided region, BP1 border position, BP2 border position,
C10 central section, P1 product pitch, P31j supply pitch,
L31j predetermined pitch

The invention claimed is:

1. A method of manufacturing an absorbent article including an absorbent main body, a pair of first side flaps and a pair of second side flaps, the absorbent main body having an absorbent body that absorbs fluid, the absorbent main body being placed against the crotch of a wearer, the pair of first side flaps being provided at one end section of the absorbent main body in a longitudinal direction, the first side flaps being folded in an outwardly projectable manner in a width direction of the absorbent main body from respective end edges of the absorbent main body in the width direction, the pair of second side flaps being provided at the other end section of the absorbent main body in the longitudinal direction, the second side flaps being folded in an outwardly projectable manner in the width direction of the absorbent main body from respective end edges of the absorbent main body in the width direction, the method comprising:
    forming a pair of side flap-folded sections by folding a continuous sheet in such a manner that end sections in a width direction of the continuous sheet are folded inwardly in the width direction, respectively, while the continuous sheet that is a base material of the first side flap and the second side flap is being transported in a continuous direction of the continuous sheet;
    producing a flap segment by segmenting the continuous sheet at a predetermined pitch in the continuous direction, the continuous sheet having the pair of side flap-folded sections formed thereon;
    joining the flap segment to a continuous body of absorbent main bodies in an overlapped manner with the flap segment lying across a border position between the absorbent main bodies adjacent to each other in the transport direction, while the continuous body that includes the absorbent main bodies continuing in the longitudinal direction is being transported in a transport direction that corresponds to a continuous direction of the continuous body; and
    dividing the flap segment into a section having the pair of first side flaps and a section having the pair of second side flaps by segmenting the continuous body of absorbent main bodies at the border position with the flap segment being joined to the continuous body of absorbent main bodies,
    wherein the pair of side flap-folded sections is formed in such a manner that a gap is provided between the side flap-folded sections regarding the width direction and that the side flap-folded sections open to a side opposite to the continuous body of absorbent main bodies, and
    wherein the method further comprises, between the forming of the side flap-folded sections and the producing of the flap segment, providing a hook member of a fastening tape in correspondence with each side flap-folded section of the pair of side flap-folded sections,
    the hook member being protruded up to a position in the gap that is inner to the side flap-folded section in the width direction,
    the side flap-folded section being constrained in a folded state by an engagement of the hook member to a portion of the flap segment that is facing the gap.

2. A method of manufacturing an absorbent article according to claim 1, wherein,
    in the joining of the flap segment to the continuous body of absorbent main bodies in an overlapped manner,
        the flap segment is joined to the continuous body of absorbent main bodies with each side flap-folded section of the pair of side flap-folded sections being made to correspond to each end section of the absorbent main body in a width direction, and
        the size of the flap segment in the width direction in a contracted width state in which the side flap-fold sections are folded is smaller than the size of the continuous body of absorbent main bodies in the width direction.

3. A method of manufacturing an absorbent article according to claim 1, wherein,
    between the forming of the side flap-folded sections and the producing of the flap segment, faces that overlap each other at the side flap-folded section are temporarily joined in such a manner that the side flap-folded section is maintained in a folded state.

4. A method of manufacturing an absorbent article according to claim 1, wherein,
    the fastening tape includes a band-like tape base material and the hook member that is secured on the tape base material,
    the fastening tape before usage being a connected body in which the tape base material of one of the folded sections of the pair of side flap-folded sections and the tape base material of the other of the folded sections are connected in a width direction via perforations, and
    wherein, in the providing of the hook member of the fastening tape, the connected body is placed across the pair of side flap-folded sections and both end sections of the connected body being joined to the side flap-folded sections, respectively, a pair of the hook members being engaged at a position of the flap segment that faces the gap.

5. A method of manufacturing an absorbent article according to claim 1, wherein,
    the absorbent body includes a fluid absorbent fiber as a main material, the continuous body of absorbent main bodies including a back surface sheet member that continues in the transport direction, the absorbent main bodies arranged on one face of the back surface sheet member intermittently in the transport direction, and a front surface sheet member that covers the other face of the back surface sheet member and provided for each of the absorbent body, the back surface sheet member including an unprovided region in which the front surface sheet member is not provided, the unprovided region being situated between the absorbent bodies that are adjacent to each other, and wherein, in the joining of the flap segment to the continuous body of absorbent main bodies in an overlapped manner, the flap segment is joined to the unprovided region with the flap segment covering each end edge of a pair of front surface sheet member that is adjacent to the unprovided region.

6. A method of manufacturing an absorbent article according to claim 5, wherein, in the joining of the flap segment to the continuous body of absorbent main bodies in an overlapped manner, the flap segment is provided in such a manner that the flap segment covers a longitudinal end section of the absorbent body, a pocket section that opens toward the end section of the absorbent body being formed on the flap segment by setting a joining region to the continuous body of absorbent main bodies on the flap segment in such a manner that the joining section surrounds the end section of the absorbent body from three directions in a U-shape.

7. An apparatus that manufactures an absorbent article including an absorbent main body, a pair of first side flaps and a pair of second side flaps, the absorbent main body having an absorbent body that absorbs fluid, the absorbent main body being placed against the crotch of a wearer, the pair of first side flaps being provided at one end section of the absorbent main body in a longitudinal direction, the first side flaps being folded in an outwardly projectable manner in a width direction of the absorbent main body from respective end edges of the absorbent main body in the width direction, the pair of second side flaps being provided at the other end section of the absorbent main body in the longitudinal direction, the second side flaps being folded in an outwardly projectable manner in the width direction of the absorbent main body from respective end edges of the absorbent main body in the width direction, the apparatus comprising:

a first device that forms a pair of side flap-folded sections by folding a continuous sheet in such a manner that end sections in a width direction of the continuous sheet are folded inwardly in the width direction, respectively, while the continuous sheet that is a base material of the first side flap and the second side flap is being transported in a continuous direction of the continuous sheet;

a second device that produces a flap segment by segmenting the continuous sheet at a predetermined pitch in the continuous direction, the continuous sheet having the pair of side flap-folded sections formed thereon;

a third device that joins the flap segment to a continuous body of absorbent main bodies in an overlapped manner with the flap segment lying across a border position between the absorbent main bodies adjacent to each other in the transport direction, while the continuous body that includes the absorbent main bodies continuing in the longitudinal direction is being transported in a transport direction that corresponds to a continuous direction of the continuous body; and a fourth device that divides the flap segment into a section having the pair of first side flaps and a section having the pair of second side flaps by segmenting the continuous body of absorbent main bodies at the border position with the flap segment being joined to the continuous body of absorbent main bodies, wherein the pair of side flap-folded sections is formed in such a manner that a gap is provided between the side flap-folded sections regarding the width direction and that the side flap-folded sections open to a side opposite to the continuous body of absorbent main bodies, and wherein between the forming of the side flap-folded sections and the producing of the flap segment, a hook member of a fastening tape is provided in correspondence with each side flap-folded section of the pair of side flap-folded sections, the hook member being protruded up to a position in the gap that is inner to the side flap-folded section in the width direction, the side flap-folded section being constrained in a folded state by an engagement of the hook member to a portion of the flap segment that is facing the gap.

* * * * *